United States Patent
Cohen et al.

[19]

[11] Patent Number: 5,957,605
[45] Date of Patent: Sep. 28, 1999

[54] CONTAINMENT AND APPLICATION DEVICE FOR LIQUID, SEMI-LIQUID, SOLID AND SEMI-SOLID PRODUCTS AND METHOD OF MANUFACTURING SAME

[75] Inventors: Roger Blair Cohen, Lakewood, Colo.; Thomas Wills, DeLand, Fla.

[73] Assignee: Gliders, Inc., Denver, Colo.

[21] Appl. No.: 08/947,294

[22] Filed: Oct. 8, 1997

[51] Int. Cl.[6] ............................................. B03C 21/00
[52] U.S. Cl. ..................... 401/132; 401/133; 401/196; 604/3
[58] Field of Search .................. 401/132–135, 401/196; 604/3

[56] References Cited

U.S. PATENT DOCUMENTS

| | | | |
|---|---|---|---|
| 2,790,982 | 5/1957 | Schneider | 401/132 X |
| 2,946,154 | 7/1960 | Bornemann | 401/196 X |
| 3,196,478 | 7/1965 | Baymiller et al. | 401/132 |
| 3,366,112 | 1/1968 | Antonik | 128/268 |
| 3,466,131 | 9/1969 | Arcudi | 401/132 |
| 3,635,587 | 1/1972 | Giesman et al. | 416/97 |
| 3,636,922 | 1/1972 | Ketner | 401/132 X |
| 3,826,259 | 7/1974 | Bailey | 401/132 X |
| 3,891,331 | 6/1975 | Avery . | |
| 4,084,910 | 4/1978 | LaRosa . | |
| 4,171,171 | 10/1979 | Jones | 401/196 X |
| 4,183,684 | 1/1980 | Avery, Jr. | 401/133 |
| 4,291,697 | 9/1981 | Georgevich | 128/269 |
| 4,475,835 | 10/1984 | Verboom et al. | 401/132 |
| 4,596,481 | 6/1986 | Tanaka | 401/132 |
| 4,643,725 | 2/1987 | Schlesser et al. . | |
| 4,878,775 | 11/1989 | Norbury et al. | 401/132 |
| 4,893,956 | 1/1990 | Wojcik . | |
| 4,899,739 | 2/1990 | Konishi | 128/156 |
| 5,046,608 | 9/1991 | Laipply | 401/132 X |
| 5,090,832 | 2/1992 | Rivera et al. | 401/138 |
| 5,380,110 | 1/1995 | Festa | 401/132 |

FOREIGN PATENT DOCUMENTS

| | | | |
|---|---|---|---|
| 677 945 | 9/1966 | Belgium . | |
| 0 294 189 | 12/1988 | European Pat. Off. . | |
| 1 142 591 | 9/1957 | France . | |
| 2 359 589 | 2/1978 | France . | |
| 2058139 | 5/1972 | Germany | 401/132 |
| WO 94/13352 | 6/1994 | WIPO . | |

*Primary Examiner*—David J. Walczak
*Assistant Examiner*—Kathleen J. Prunner
*Attorney, Agent, or Firm*—Duft, Graziano & Forest, P.C.

[57] ABSTRACT

This invention pertains to a device and the method of making same, which device functions both as a containment system for a product having either liquid, semi-liquid, solid or semi-solid characteristics, and as an applicator that can be used to deliver and apply the product to a surface in a convenient, economical and simple manner. The device includes an applicator pad that has a front surface that comes in contact with the desired surface to thereby apply the product thereto. A product impermeable backing layer is bonded to a rear surface of the applicator pad and a packet can be placed in position to release the product into the applicator pad through an aperture formed in the backing layer. A multi-purpose label is used to seal the packet in place, protects the user's hands, provides printed information to the user, provides the user with a device gripping surface and can also function to seal and/or reseal the applicator device. The label therefore can perform the important function of protecting the user from contact with products that are undesirable or irritating to the skin. Thus, the manufacture proceeds in two phases: assembly of the basic device absent the product; final filling of the device with the product and labeling with the multi-purpose label.

30 Claims, 7 Drawing Sheets

CONTAINMENT AND APPLICATION DEVICE FOR LIQUID, SEMI-LIQUID, SOLID AND SEMI-SOLID PRODUCTS AND METHOD OF MANUFACTURING SAME

FIELD OF THE INVENTION

This invention pertains to a device and the method of making same, which device functions both as a containment system for a product having either liquid, semi-liquid, solid or semi-solid characteristics, and as an applicator that can be used to deliver and apply a unit dose of the product to a surface. This device can be assembled and later filled with the product to thereby reduce inventory costs.

PROBLEM

It is a problem in the field of liquid, semi-liquid, solid and semi-solid products to provide an economical applicator system for containing and dispensing a product in a convenient, uniform and simple manner on to a surface. The applicator system must be economical and simple to manufacture, especially when the applicator system is directed to the field of a single-use or a limited number of uses product application. A further problem is that the product filled applicator represents a significant inventory cost and can represent a significant write down to the manufacturer if the shelf life of the product is exceeded.

Many liquid, semi-liquid, solid and semi-solid products can be applied to the desired surface by the user simply placing the product on their hand from a container and then manually spreading the product on the desired surface. Examples of such products are personal care products such as: sunscreen lotions, insect repellant, skin lotion, makeup, and the like; medical care products, such as: topical lotions, medicated creams, and the like; sports products such as: muscle heat ointments, eye black, anti-fogging coatings for lenses and the like and other products that can be abusive and irritating to the skin. The manual method of product application is the most inexpensive applicator system, but is also inefficient, messy, and may result in nonuniform application of the product to the desired surface. The product containers are also typically designed for multiple uses and therefore contain a fairly large quantity of the product, making the containers inconvenient to carry with the user. This quantity of product also may result in waste of the unused portion of the product. A further problem with this system is that the product is typically contained in a jar, tube or bottle and is subject to spillage. For many of the products dispensed in this manner, it is undesirable to have a residue remain on the user's hands and the user must therefore have a mechanism available to clean their hands once the product has been applied to the desired surface.

To avoid the problems noted above, the liquid, semi-liquid, solid and semi-solid products can be applied to the desired surface by the use of a separate applicator element which the user must place in contact with the product. The applicator soaks up a quantity of the product from a product container and the user then holds the product containing applicator in their hand to spread the product on the desired surface. As noted above, the product containers are typically designed for multiple uses and therefore contain a fairly large quantity of the product, making the containers inconvenient to carry with the user. This quantity of product also may result in waste of the unused portion of the product. A further problem with this system is that the product is typically contained in a jar, tube or bottle and is subject to spillage. A further problem with this system is that even with the use of the applicator, the product may come in contact with the user's skin, especially the user's hands. The user must therefore have a mechanism available to clean their hands once the product has been applied to the desired surface.

In order to avoid these above-noted problems, a number of self-contained applicator devices have been designed by product manufacturers to dispense a variety of products for a limited number of uses product application. These self-contained applicator devices dispense a limited quantity of the product. These self-contained applicator devices can be divided into two general categories of product application: product application via spreading on a surface area, and medicament application to a limited size, fixed site on a patient's skin.

In the field of general use products, the self-contained applicator devices are exemplified by the teaching of the following patents.

U.S. Pat. No. 3,466,131 discloses a dispensing package that comprises an applicator pad of porous material which is sealed to the underside of a housing. The housing encloses a rupturable capsule that contains the material to be dispensed. The liquid flow from the rupturable capsule to the pad is directed by channels formed in the housing.

U.S. Pat. No. 4,291,697 discloses a cleaning and applicator device used for medical purposes. The device comprises a handle attached to a packaged sponge that encloses a rupturable pouch that contains the liquid. The pouch is manually ruptured by the application of pressure and the user manipulates the applicator device by means on the handle.

U.S. Pat. No. 4,475,835 discloses a device for cleaning soil from oven surfaces and comprises a reservoir having a rupturable membrane covering the open mouth of the reservoir. An abrasive cleaning pad also covers the open mouth of the reservoir, through which the cleaning solution flows once the reservoir covering is ruptured.

U.S. Pat. No. 4,596,481 discloses a sheet assembly for polishing work which comprises a fabric sheet bonded to a non-permeable sheet to define a first chamber. A rupturable capsule is placed in this chamber and the liquid contained therein flows through openings formed in the non-permeable sheet to spread the liquid on the applicator surface.

U.S. Pat. No. 4,878,775 discloses a liquid transfer device which comprises a support layer bonded to a permeable applicator pad to form a chamber in which is placed a carrying substrate filled with frangible microcapsules containing the liquid to be applied. The compression of the carrying layer ruptures the microcapsules and releases the liquid through the applicator pad.

U.S. Pat. No. 5,090,832 discloses a disposable cleaning pad comprising a scrubable layer of porous material bonded to a non-permeable sheet to define a first chamber. A rupturable capsule is placed in this chamber and the liquid contained therein flows through openings formed in the non-permeable sheet to spread the liquid on the applicator surface.

These above-noted self-contained applicator devices all partially solve the problem of manual application of a product to a desired surface. These self-contained applicator devices all comprise a liquid containment vessel, either a reservoir or a rupturable bladder, that is located juxtaposed to an applicator pad. An impermeable membrane separates the applicator pad from the user's hand or the exposed surface of the applicator to prevent spread of the liquid in an undesirable direction. A problem with all of these self-contained applicator devices is that they are fairly expensive to manufacture and, in many cases, are directed to a specific liquid product application, where the nature of the product justifies the increased applicator cost. In addition, some of these architectures are inapplicable to certain types of products due to the potential reactivity of the product with the packaging materials and/or the potential for inadvertent release of a product.

A more significant problem with self-contained applicator devices is that the manufacturing processes for these self-contained applicator devices require the insertion of the rupturable bladder into the self-contained applicator device or the filling of the reservoir formed in the self-contained applicator device prior to the bonding of the applicator pad to the housing or impermeable membrane. Thus, the self-contained applicator device must be carefully handled during the manufacturing process to prevent spillage of the product and this spillage avoidance increases the cost of manufacture. In addition, the self-contained applicator device is manufactured in its entirety, with product included therein. The inclusion of the product in the self-contained applicator devices results in significant inventory capital and carrying costs to the manufacturer, in many cases in excess of 10% per year additional cost, and also can result in significant write down costs. This write down cost factor is complex and represents the cost of many different marketing, distribution and sales problems. One such example is that many retail distribution outlets will not accept product with less than a predetermined remaining shelf life due to their own internal delays in moving the product to sale and the write down process comprises complete destruction of the product with no salvage value. Thus, the effective shelf life of a product can be far less than its nominal expiration date. Furthermore, seasonal and geographic variations in demand can result in expensive express shipment of inventory to meet these needs. Thus, maintaining an adequate yet cost effective inventory of product filled self-contained applicator devices is a difficult and costly problem to manage.

In the medicament application category, the product to be dispensed is a medicament and the constraints on the self-contained applicator devices are far more stringent than for general use products. The issues of contamination of the applicator, shelf life of the product, interaction of the medicament with the self-contained applicator device, and the like, are issues that must be addressed by the applicator manufacturer. As an example of the state of the art in the medicament dispensing field, the following patents teach the provision of a bandage system that also serves as the medicament dispensing element.

U.S. Pat. No. 3,366,112 discloses an adhesive bandage having a container of liquid medicament contained therein. When the user removes the protective layers to expose the adhesive portion of the bandage, the rupturable pouch that contains the medicament is exposed and can be ruptured to release the medicament on to a pad that comes in contact with the patient's skin.

U.S. Pat. No. 4,899,739 discloses an adhesive bandage comprising a pad for absorbing a medicine which is stored in a rupturable capsule. When the user removes the protective layers to expose the adhesive portion of the bandage, the rupturable pouch that contains the medicament is exposed and can be ruptured to release the medicament on to a pad that comes in contact with the patient's skin.

U.S. Pat. No. 3,826,259 discloses a self-contained disposable swab-type medication applicator that comprises a rigid reservoir housing adapted to receive a liquid, with a removable strip closing the open mouth of the reservoir. An applicator pad covers a portion of the reservoir and receives the liquid through a rupturable aperture formed in the housing. Once the removable strip is removed to expose both the reservoir and the applicator pad, the liquid flows from the reservoir to impregnate the applicator pad.

These medicament dispensing systems have similar limitations to the general self-contained applicator devices noted above. In addition, since these self-contained applicator devices dispense medicaments, they are highly regulated to ensure patient safety. The safety issues considered in this process include the possibility of infection transmission by use of the self-contained applicator devices, potential for contamination of the medicament or applicator device prior to use, the controlled application of the medicament to provide a medically effective treatment, availability of a container and applicator in unit dose form, the safety of the self-contained applicator device in that the medicament and the packaging materials are non-reactive together and the packaging of the medicament ensures the designated shelf life of the medicament. Therefore, medicament dispensing self-contained applicator devices largely rely on the use of a rupturable bladder that contains the medicament. The packaging materials used to form the bladder are selected to be non-reactive with the medicament and the resultant bladder is designed to be secure from leakage or contamination of its contents. The process to design, test and obtain approval of the product containing bladder, and the self-contained applicator device that uses the product containing bladder can be very expensive and time consuming. The medicament dispensing systems noted above use rupturable bladders to dispense the medicaments, but they are in the form of an adhesive bandage which provides no spreading capability, and are exclusively designed for single site contact application.

In summary, the basic problem with the above-noted self-contained applicator devices is that they are a relatively expensive product delivery system given the limited quantity of product dispensed. In addition, these applicator devices don't always ensure that the product does not get on the user's hands, and in turn, that the user's hands don't come in contact with the surface where the product will be applied. These applicator devices are typically custom designed for each product, with the manufacturer expending significant expenses and time to develop, test and eventually manufacture the applicator devices. These applicator devices must also be manufactured in their entirety and filled with product, which raises the cost of the product due to the need to manufacture and inventory completely assembled and filled applicator devices. Further, this problem typically replicates for each product sold in a self-contained applicator device throughout the product distribution network. At the point in time when inventory has not sold in the allotted time-frame, that inventory is frequently thrown away in bulk. This not only compounds the financial burdens of that inventory, which is passed on to the consumer, but additionally, is a tremendous waste of resources. All of these additional product costs add to the ultimate cost to the consumer. These cumulative costs represent a major factor in determining whether a self-contained applicator is both feasible and economical for a limited number of use product application.

SOLUTION

The present invention pertains to a device and the method of making same, which device functions both as a containment system for a product having either liquid, semi-liquid, solid or semi-solid characteristics, and as an applicator that can be used to deliver and apply the product to a surface in a convenient, economical and simple manner. This unique containment and application device provides convenient storage and transportation of the product, particularly for the unit dose application of the product. The containment and application device is simple and economical to manufacture and need not be filled with the product until the final stage of the manufacturing process, such that generic containment and application devices can be manufactured and stored without being filled with the product until final assembly for shipping is required, thereby significantly reducing inventory and write down costs.

The present containment and application device is an applicator for liquid, semi-liquid, solid and semi-solid products which include, but are not limited to products in the form of: liquid, gel, wax, foam, oil, ointment, powder and the like. A preferred embodiment of the containment and application device includes an applicator pad that has a front surface that comes in contact with the desired surface to thereby apply the product thereto. A product impermeable backing layer is bonded to a rear surface of the applicator pad and a packet, typically containing a unit dose of the product, can be placed in position to release the product into the applicator pad through an aperture formed in the backing layer. A multi-purpose label is used to seal the packet in place, protects the user's hands, provides printed information to the user, provides the user with a device gripping surface and can also function to seal and/or reseal the applicator device. The label therefore can perform the important function of protecting the user from contact with products that are undesirable or irritating to the skin, such as: hemorrhoid cream, insect repellant, anti-fungal cream, automotive products, sunless tanning products, and the like. Thus, the manufacture of the present containment and application device is simple and can proceed in two phases: assembly of the basic device absent the product; final filling of the device with the product and labeling with the multi-purpose label. The inventory costs of the containment and application device are drastically reduced by this ability to bifurcate the assembly process and avoid having to warehouse the containment and application devices with the product included therein.

The present containment and application device is therefore architected to be inventoried after manufacturing, or shipped to a multitude of companies that manufacture a diverse set of products for filling and labeling, or can proceed in-house directly to filling and labeling. In the instance where devices are shipped to outside companies, the unfilled and unlabeled devices can be inventoried until such time as orders are received. This process reduces the capital and carrying costs of inventory, and reduces the waste of fully manufactured unused inventory. Further advantages to companies using the present containment and application device are that for a broad spectrum of products, they need only inventory a common shared pool of generic unfilled and unlabeled containment and application devices, instead of inventorying multiple types of product filled applicator devices. Consumers benefit from lower product costs, convenient self-contained applicator devices for many products, and the advantage of a system where the consumer can apply products to many different types of surfaces without getting the product on their hands or directly contacting the surface to which the product is applied. In addition, the multi-purpose label functions as a label, a primary sealing mechanism, secondary sealing mechanism, impermeable membrane, handle, support for display, and thereby greatly decreases the manufacturing costs of the completed, filled and labeled device.

DETAILED DESCRIPTION

In the field of self-contained applicator devices, the applicator device attempts to ensure that the user perceives the delivery system as convenient to use and the quantity of product delivered as economically justified. The self-contained applicator device also must be convenient for the user to carry with them and simple to display in a retail environment. The architecture of the self-contained applicator device must address these requirements and minor variations in the architecture can have profound effects on the cost and simplicity of manufacture of the self-contained applicator device.

Basic Product Containment and Application Device

Figure 1A:
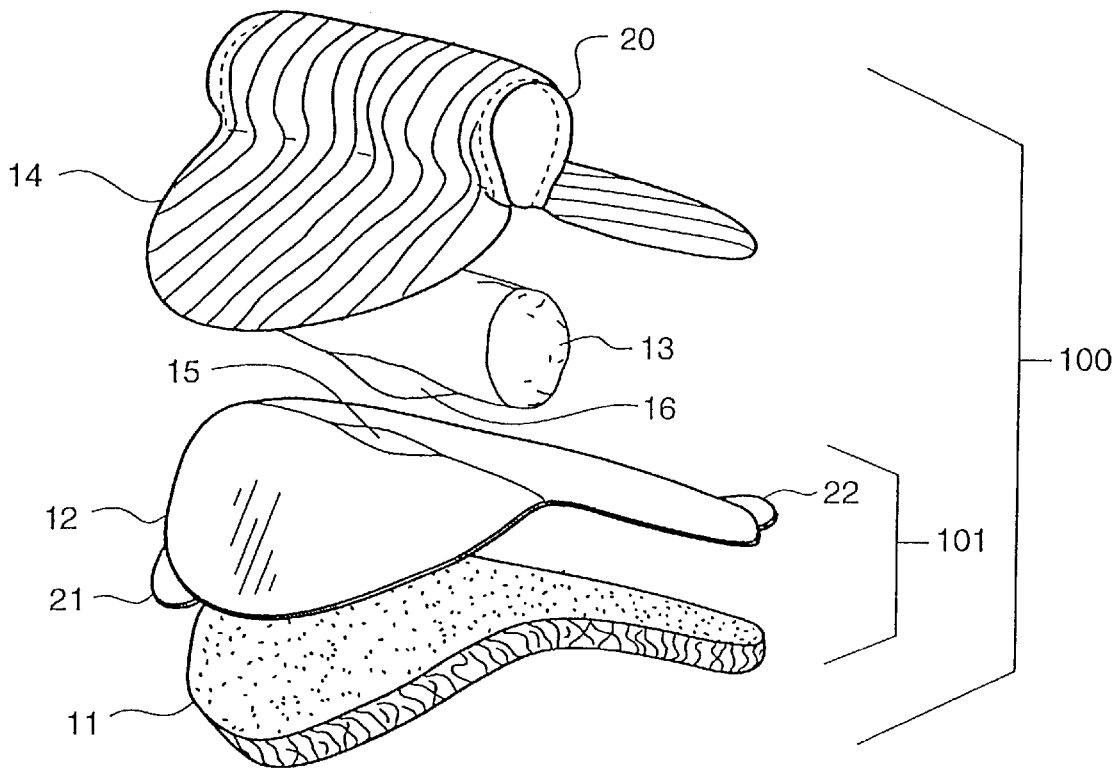
FIGS. 1A & 1B illustrate a perspective exploded view and a perspective view, respectively, of the present containment and application device.
Figure 1B:
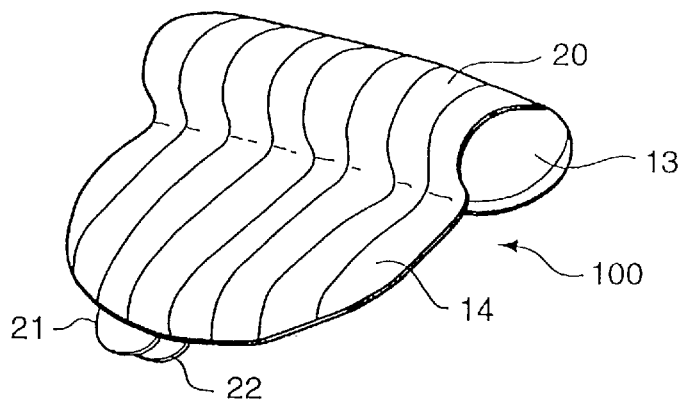

FIGS. 1A & 1B illustrate a perspective exploded view and a perspective view, respectively, of a preferred embodiment of the present containment and application device 100, which is illustrated as a substantially cylindrically shaped device comprised of four individual elements. The shape illustrated in FIGS. 1A & 1B is selected due to simplicity of implementation of the collapsible version of the containment and application device, although any solid geometric or arbitrary shape can be used. The basic characteristics of the containment and application device 100 that are of concern include, but are not limited to:

1. Meets government regulatory standards (if any)
2. Inexpensive to manufacture
3. Functions to apply product simply
4. Functions to apply product uniformly
5. Disposable single-use or limited-use system
6. Protects the user from contact with the product
7. Device is sized to be convenient to carry The essential element of containment and application device 100 is the storage and delivery element 101 which comprises the applicator pad 11 that functions as the instrumentality to apply the product to the desired surface, to which is bonded a impermeable backing element 12. The applicator pad 11 has a front surface which contacts the surface that receives the product and a back surface to which is bonded the impermeable backing element 12 that functions to prevent migration of the product from the applicator pad 11 to the user's hand. The product can be placed into the storage and delivery element 101 in a number of ways. The applicator pad 11 can function to store the product as input through a hole 23 formed in the backing element (FIG. 3) or can be supplied (via an aperture 15 shown in FIG. 1A) with product from a packet 13. The packet 13 can be located behind the impermeable backing element 12 or in the handle portion 20 of the label 14 and comprises a product containment vehicle that is operable to controllably release the product into the applicator pad 11. The user causes either a controlled breakage of the packet integrity or operation of a nozzle 16 contained in the packet 13 to cause the product to pass from the packet 13 to the applicator pad 11 via an aperture 15 formed in the impermeable backing element 12. A integral handle 20 is provided on the containment and application device 100 to provide a surface which the user can grip to manipulate the containment and application device 100. Optional pull apart tabs 21, 22 are provided to enable the user to switch the containment and application device 100 from the closed clamshell state illustrated in FIG. 1B to the deployed state, illustrated in exploded view form, in FIG. 1A.

While a specific configuration of elements are illustrated in FIGS. 1A & 1B, it is obvious that numerous variations are possible. The present version of the containment and application device 100 is described to illustrate the underlying concepts of the device.

Alternate Configurations and Features

Figure 2:
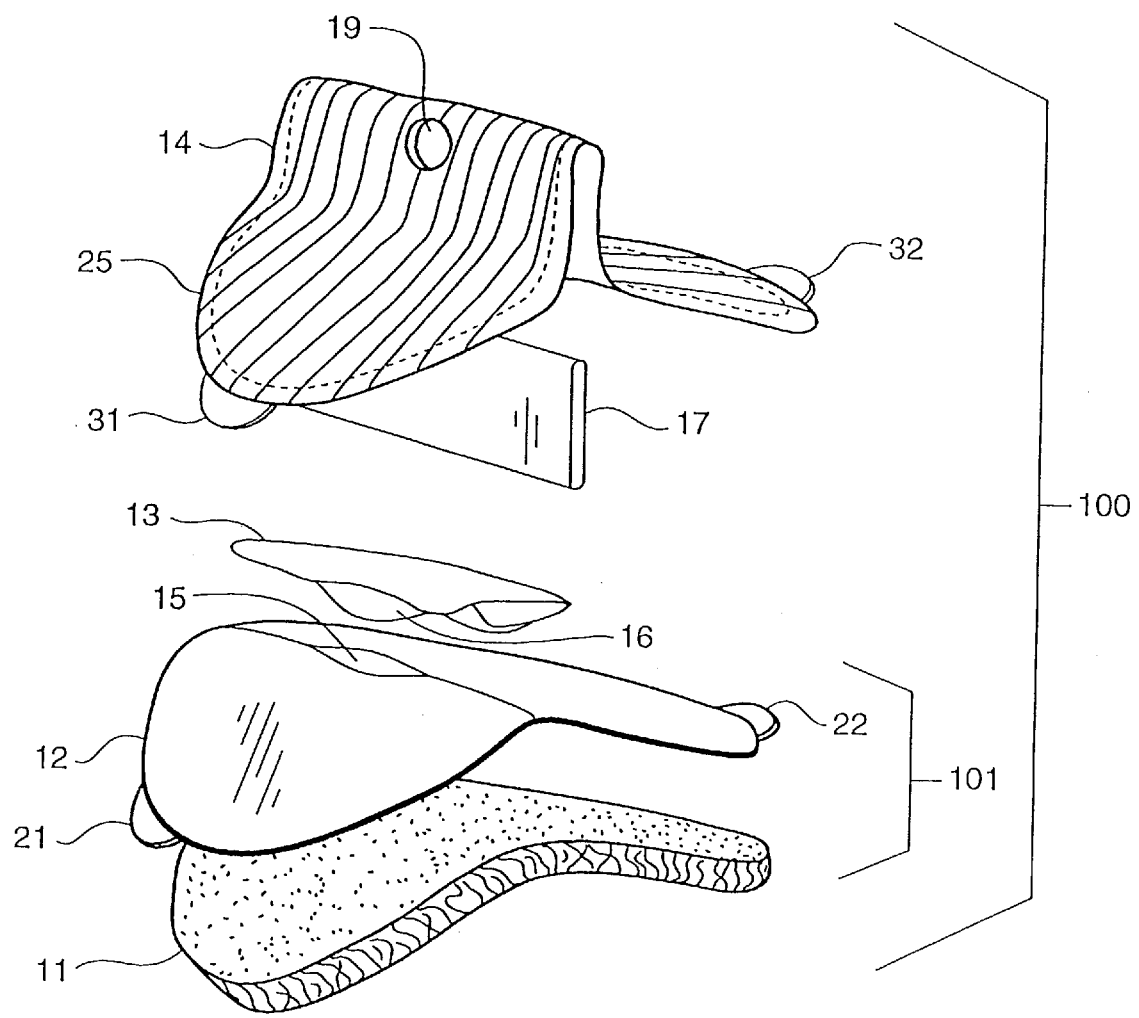
FIGS. 2–4 illustrate perspective exploded views of alternate implementations of the present containment and application device.
Figure 3:
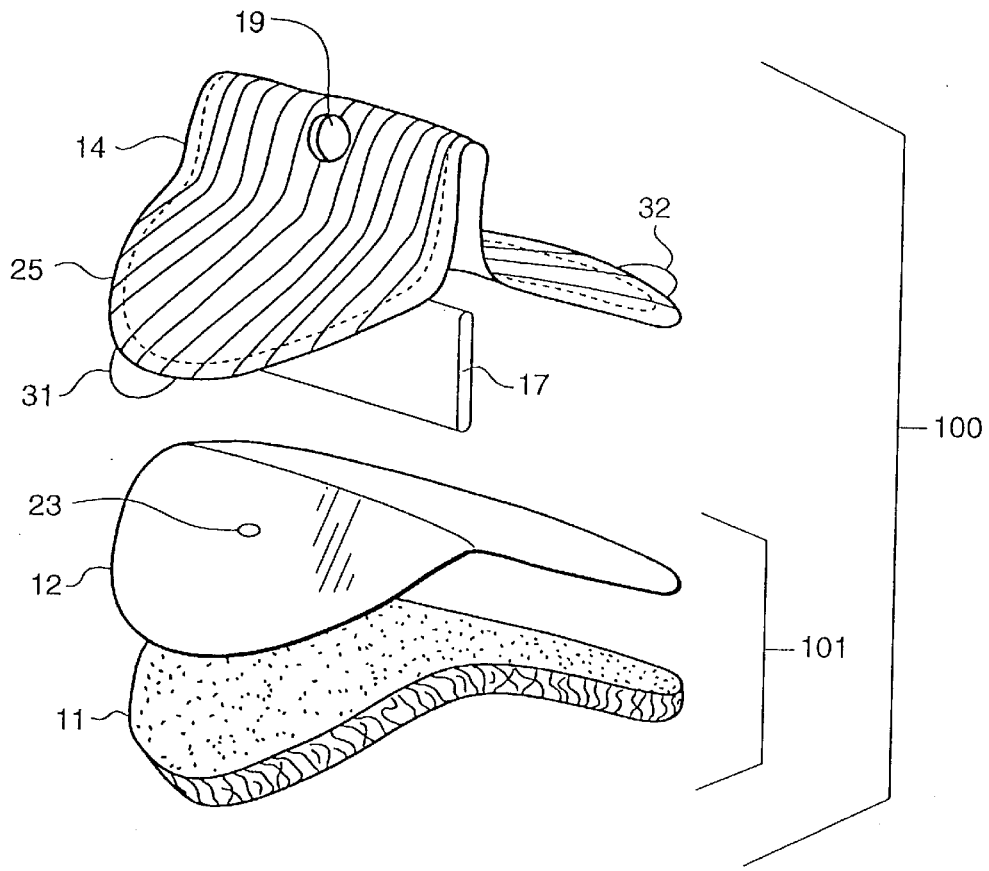
Figure 4:
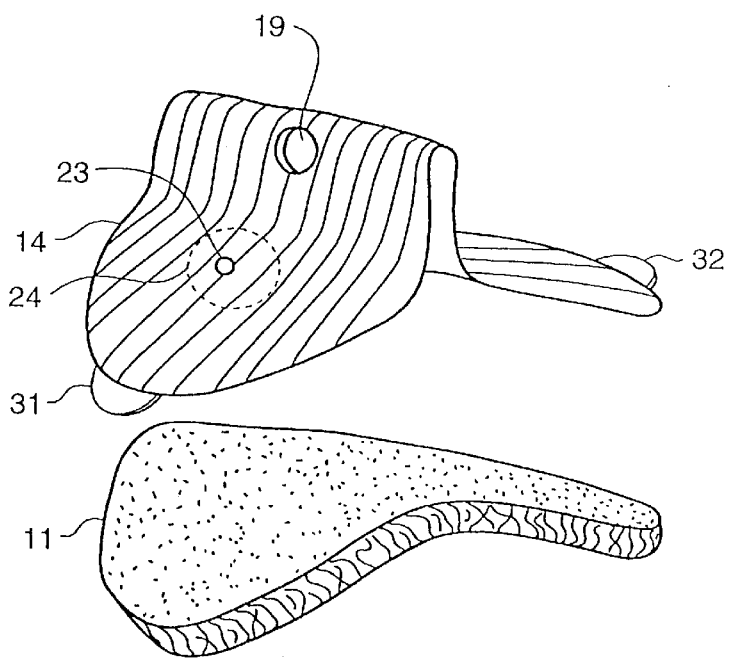

FIGS. 2–4 illustrate perspective exploded views of alternate implementations of the present containment and application device 100. In particular, FIG. 2 illustrates the containment and application device 100 of FIG. 1 with the addition of an optional stiffener element 17 that can be used to provide a rigid handle surface, formed of the label 14 applied to the stiffening element 17. There can also be the inclusion of a hole 19 formed in the handle 20 to enable the containment and application device 100 to be placed on a product display where the containment and application device 100 is hung on a display rod or hook by means of the hole 19. Furthermore, the packet 13 can be insertable through the aperture 15 to thereby occupy the space between the impermeable backing element 12 and the applicator pad 11, with the label 14 sealing the aperture 15 once the packet 13 is inserted through the aperture 15. The sealing of the containment and application device 100 into the clamshell configuration can be accomplished by the use of a label 14 that has dimensions greater than the underlying applicator pad 11 and impermeable backing element 12. Thus, when applied to the exposed surface of the impermeable backing element 12, a rim 25 of the label 14 extends beyond the periphery thereof and adheres to itself when the containment and application device 100 is folded into the clamshell configuration. In this mode, the user can separate the label 14 from itself, thereby deploying the containment and application device 100, by simply pulling the tabs 21, 22 apart to break the seal formed by the adhesive on the label rim 25. The optional additional tabs 31, 32 can be used to substitute for tabs 21, 22.

FIG. 3 illustrates a further embodiment wherein the use of the packet 13 is eliminated and the product is injected into the applicator pad 11 or into the space between the applicator pad 11 and the impermeable backing element 12 during the manufacturing process. Application of the label 14 to the impermeable backing element 12 then seals the hole 23 through which the product in injected and manufacture of the containment and application device 100 is completed. Another alternative is illustrated in FIG. 4 where the impermeable backing element 12 is eliminated and the label 14 performs the functions of the impermeable backing element 12 as well as the label 14. This configuration can be used to enclose the packet 13 (not shown) in contact with the applicator pad 11 or can simply enclose the applicator pad 11 when the product is injected through hole 23 in the label 14 into the applicator pad 11 and the hole 23 used to accomplish this product charging step is sealed by means of an additional label element 24 shown in dotted line form in FIG. 4.

Containment and Application Device Manufacturing Process

Figure 5:
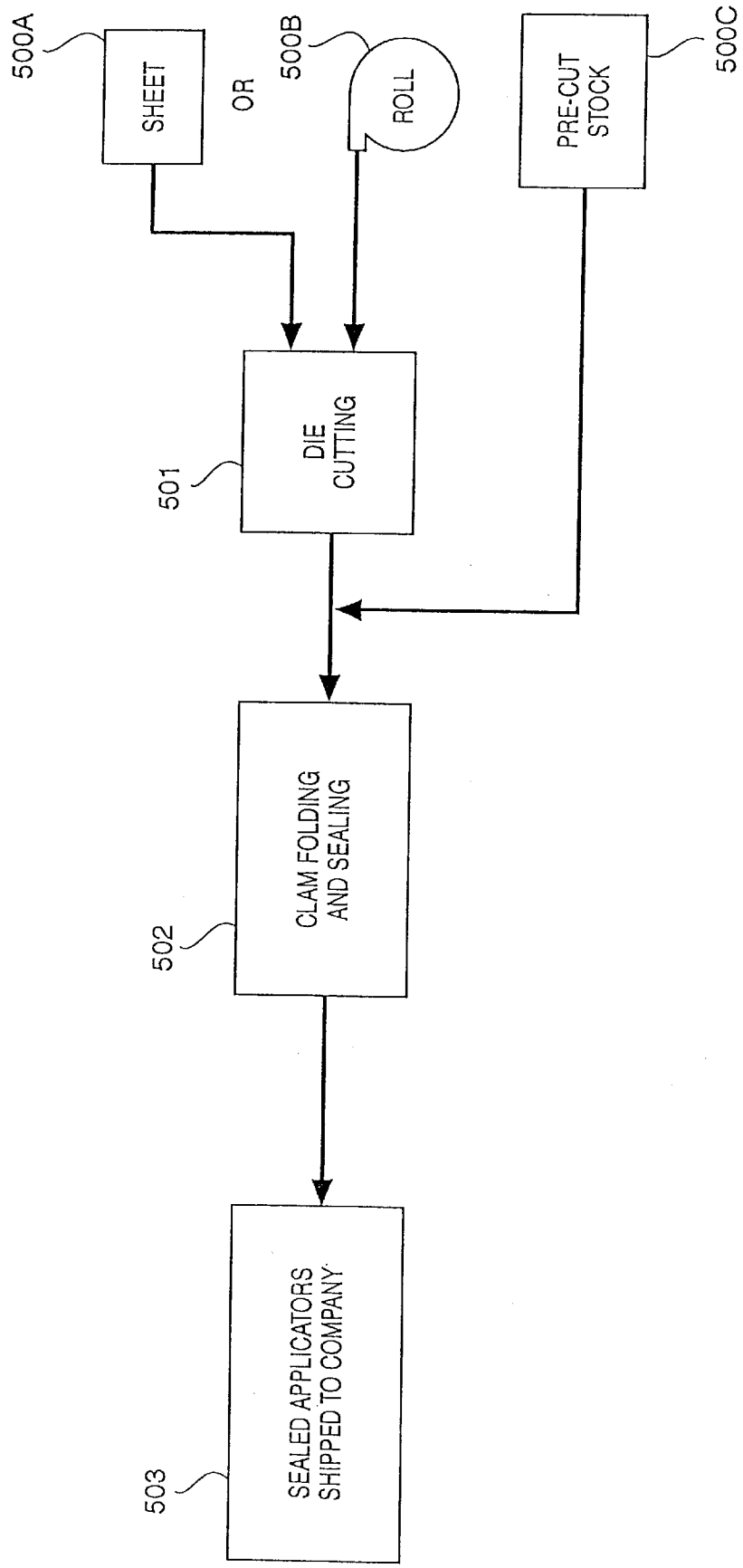
FIGS. 5 & 6 illustrate in flow diagram form the manufacturing process used to construct the present containment and application device.
Figure 6:
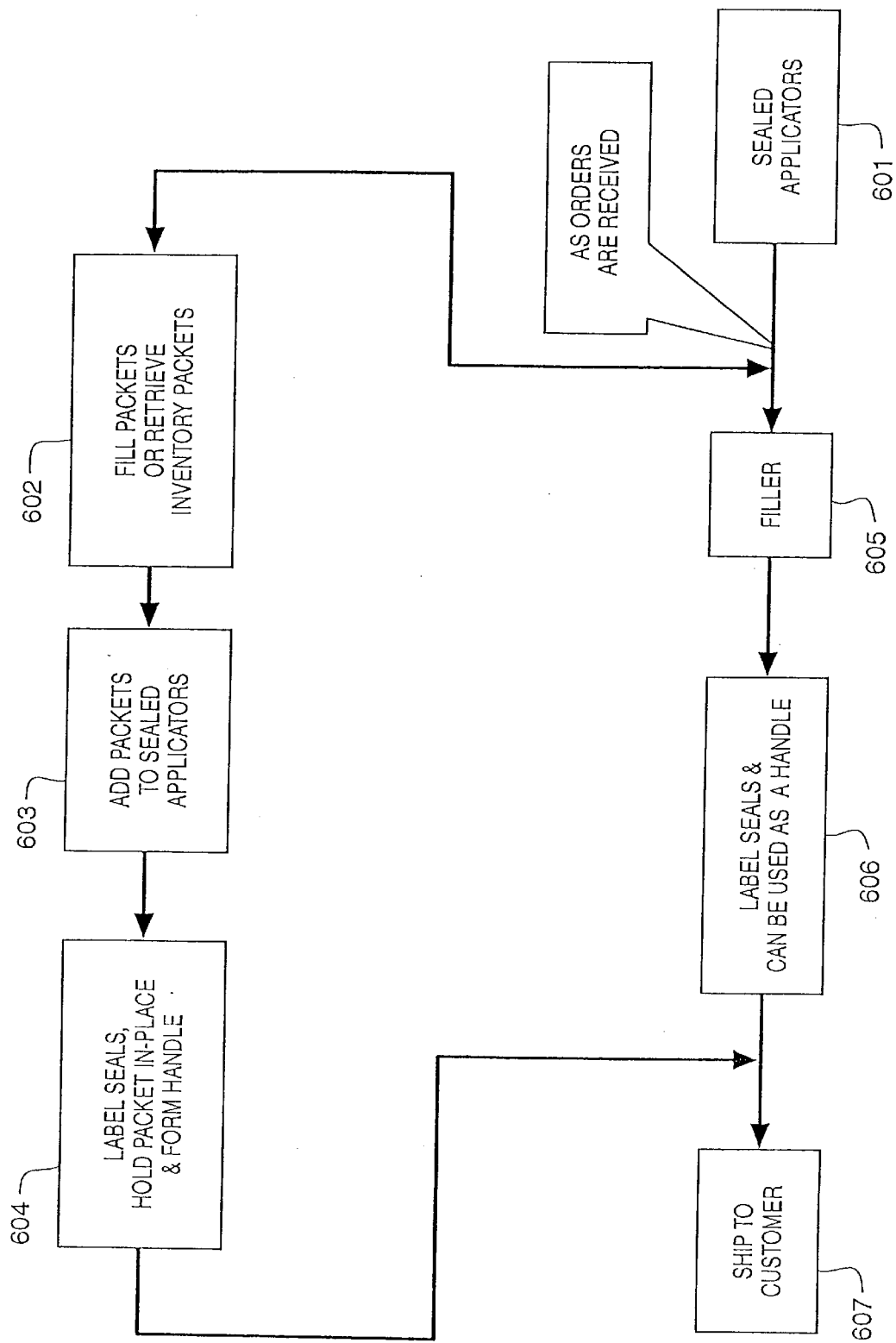

FIGS. 10A–10E illustrate perspective views of the present containment and application device 100 as it progresses through the manufacturing steps noted in FIGS. 5 and 6. In particular, as shown in FIG. 5, the raw materials used to implement the delivery element 101 can be in the form of sheet stock 500A, roll stock 500B or precut elements 500C. If these materials are sheet stock 500A, or roll stock 500B, they must proceed to process step 501 where they are die cut into the necessary size and shape. The resultant elements: applicator pad 11 and impermeable backing element 12, are then folded into a clamshell configuration and sealed together in step 502, with the resultant assembled delivery element 101 being shown in FIG. 10A. The delivery element 101 proceeds to process step 503, which is termed "shipped to company" in FIG. 5. This process step indicates that the delivery element 101 can be inventoried as noted above for future use. This can entail storing the delivery element 101 in the manufacturing facility for later use in the second portion of the manufacturing process as illustrated in FIG. 6, immediate use of the delivery element 101 in the second portion of the manufacturing process as illustrated in FIG. 6, or shipping the delivery element 101 to the company that is charged with the task of implementing the manufacturing process as illustrated in FIG. 6. In any case, the manufacturing process illustrated in FIGS. 5 and 6 can be either a continuous process or a two step process separated by any length of time.

The second portion of the manufacturing process is illustrated in FIG. 6. The delivery elements 101 are received or retrieved from storage at step 601 in response to the receipt of orders for the containment and application devices 100 or as part of a regularly scheduled manufacturing run. The manufacturing process can be implemented in either of two ways: process steps 602–604 for the packet 13 in containment and application device 100 illustrated in FIG. 1A, 1B, 2 or process steps 605–606 for the product injection version of the containment and application device 100 illustrated in FIGS. 3 & 4. In the former process, at step 602, the product containing packets 13 are filled with the desired product or retrieved from inventory. With the packets 13 and delivery elements 101, the process advances to process step 603 where the packets 13 are added to the sealed delivery elements 101. As noted above, the packets 13 can be inserted through the aperture 15 formed in the impermeable backing element 12 of the delivery element 101 to reside between the impermeable backing element 12 and the applicator pad 11, or the packet 13 can be positioned such that a nozzle 16 formed in the packet 13 is positioned to release the product from the packet 13 through aperture 15 into the applicator pad 11. In either case, the next process step is step 604 where the label 14 is applied to the exposed surface of the impermeable backing element 12 to hold the packet 13 in place as shown in FIG. 1A or to seal the aperture 15 once the packet 13 has been inserted through the aperture 15. The label 14 can form the handle 20, with the optional inclusion of a stiffening element 17. Once the label 14 has been applied, the product containing packet 13 is sealed within the containment and application device 100, with the remaining process step 607 being the packaging of the completed containment and application device 100 for shipment to the customer.

Figure 10A:
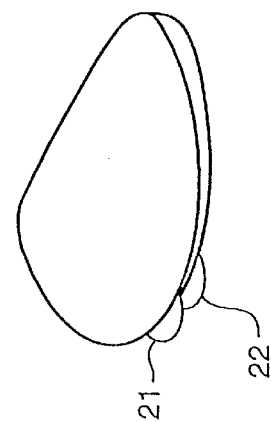
FIGS. 10A–10E illustrate perspective views of the present containment and application device as it progresses through the manufacturing steps noted in FIGS. 5 & 6.
Figure 10B:
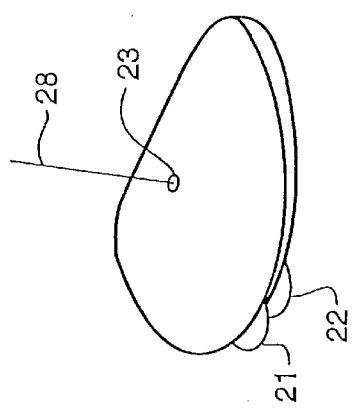
Figure 10C:
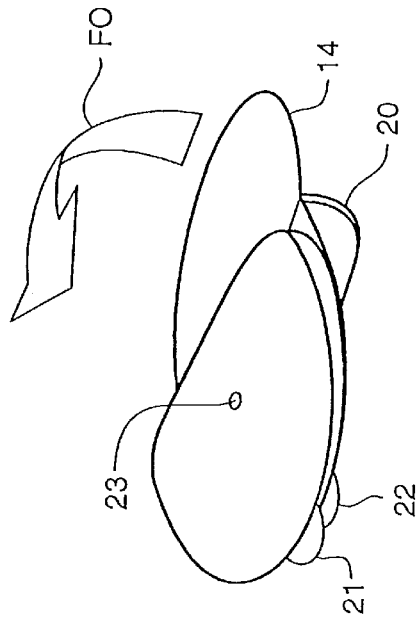
Figure 10D:
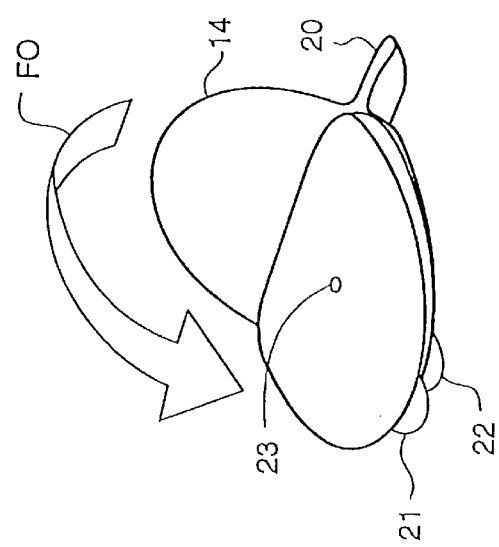
Figure 10E:
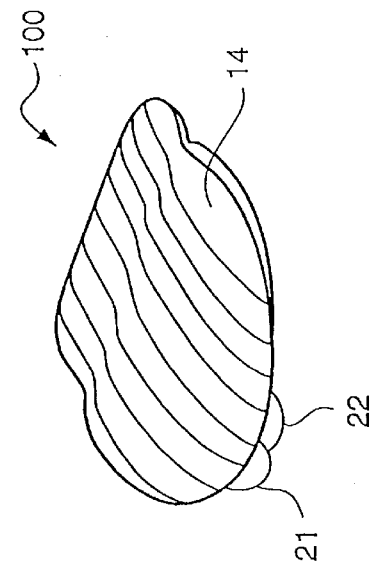

The alternative manufacturing process comprises steps 605–606 where the product is injected via needle 28 into the delivery element 101 through the hole 23 in the impermeable backing element 12 as shown in FIG. 10B. Once the applicator pad 11 has been charged with the product, processing advances to step 606 where the label 14 is applied to one of the exposed surfaces of the impermeable backing element 12 as shown in FIG. 10C. The label 14 is then folded over the delivery element 101 in the direction indicated by arrow FO to seal the aperture 23 through which the product has been injected into the applicator pad 11 as shown in FIG. 10D. The label 14 can form the handle 20, with the optional inclusion of a stiffening element 17. Once the label 14 has been applied as shown in FIG. 10E, the product is sealed within the containment and application device 100, with the remaining process step 607 being the packaging of the completed containment and application device 100 for shipment to the customer.

Deployment of the Containment And Application Device

Figure 7:
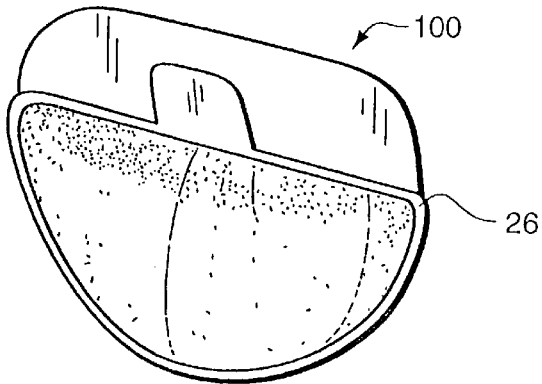
FIGS. 7–9 illustrate perspective views of the present containment and application device as it progresses from the sealed state to the deployed state.
Figure 8:
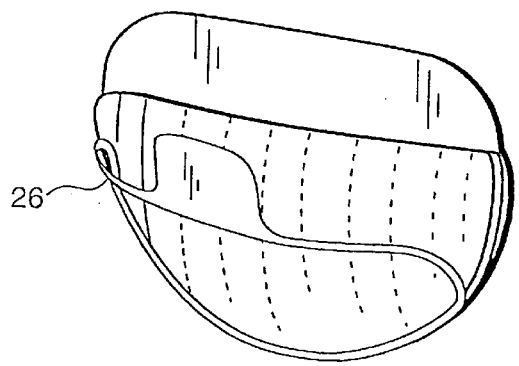
Figure 9:
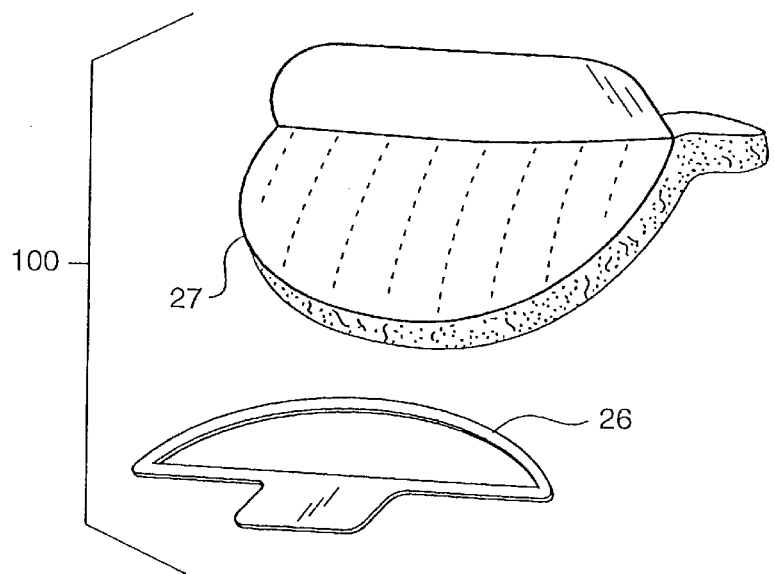

FIGS. 7–9 illustrate a perspective view of the present containment and application device 100 as it progresses from the sealed (first) state to the deployed (second) state, by removal of the retaining element 26 as illustrated in FIG. 8. As can be seen from these Figures, the body 27 of the containment and application device 100, once freed of the retaining element 26, enters the deployed (second) state which comprises the applicator pad 11 opened to form a substantially planar surface for use to apply the product to the desired surface as shown in FIG. 9.

Applicator Pad

The applicator pad 11 is constructed of a product transporting element, such as low density polyethylene, that provides a mechanism to deliver the product to the desired surface. The applicator pad can be constructed of different materials and can include multiple layers. For example, a surface layer can comprise a scour pad surface for use in cleaning dishes, with a second underlying layer comprising a "sponge-like" layer that contains dish soap. Alternatively, the soap can be retained in a liquid reservoir, as described below. The applicator pad 11 is designed to provide the proper interface for the selected use. The characteristics of the applicator pad 11 can therefore vary widely. The abrasiveness of the scour pad can be contrasted with the delicate surface of the applicator pad 11 when the containment and application device 100 is used for the delivery of personal care products. To reduce the possibility of the product being released from the applicator pad 11 in an undesirable manner, the applicator pad 11 or the impermeable backing element 12 can include a resealable capability. The resealable element can be a Velcro dot, mating dimples on the opposing surfaces of the impermeable backing element 12, or a zip strip that is integral in the outer edge of the impermeable backing element 12, or simply an adhesive strip to hold the edges together.

Typical Uses of the Device and Exemplary Products Contained Therein

The containment and application device 100 can be used to dispense a wide range of products in a diverse set of product applications. For example, the following indicates a partial list of the classes of products and exemplary products that can be packaged in the containment and application device 100:

Skin Lotions Sun
  Block
  Self-Tanning
  Moisturizing
Cosmetics
  Nailpolish Remover
  Facial Cleanser
  Powders
  Cologne
Medicaments
  Topical Lotions
  Insect Bite Medication
Sports/Recreation products
  Insect Repellant
  Eye Black
  Ski Wax
Automotive
  Hand Cleaner
  Car Wax
Veterinary products
  Fly Wipe
  Hoof Black
  Cut/Abrasion treatments
Furniture Care
  Cleaners
  Oils
  Stains
Child Care products
  Baby Wipes
  Baby powder
Household products
  Disposable pot Scrubbers
  Non-Stick Liquids
  Window Cleaner Furthermore, these various products and product categories can be distributed through many different channels of trade. For example, these products can be distributed as unit dose retail products, complimentary products for hotel/promotional use, private label products, and unit dose dispensing of prescription products.

Summary

The present containment and application device is a single-use or limited-use applicator that enables the user to apply a uniform layer of a liquid or semi-liquid product to a desired surface in a convenient, economical and simple manner. The containment and application device provides convenient storage and transportation of the product, and also provides the user with the ability to apply products to the desired surface without getting the products on the user's hands.

What is claimed:

1. An apparatus for the containment and application of a product that has a one of liquid, semi-liquid, solid and semi-solid characteristics, comprising:

means, having a front surface and a back surface, for controllable delivery of said product via said front surface;

backing means, integrally attached to said back surface to form a product receiving site juxtaposed to said back surface, for providing a substantially impermeable barrier to said product;

an aperture for enabling placement of said product into said product receiving site, formed in said backing means; and packet means for storing a predetermined quantity of said product, said packet means being at least partially insertable into said product receiving site through said aperture.

2. The apparatus of claim 1 wherein said packet means is rupturable to release said product into said product receiving site upon application of a predetermined force thereon by a user.

3. The apparatus of claim 1 wherein said packet means stores a predetermined quantity of said product, and has a nozzle means for liquid communication through said aperture between an interior of said packet means and said means for controllable delivery, operable to enable passage of said product from said interior of said packet means to said means for controllable delivery in response to activation by said user.

4. The apparatus for the containment and application of a product of claim 1 further comprising:

means for covering said aperture to prevent release of said product from said product receiving site.

5. The apparatus for the containment and application of a product of claim 4 wherein said means for covering comprises:

label means for substantially covering said backing means.

6. The apparatus for the containment and application of a product of claim 4 wherein said means for covering further comprises:

label means for substantially covering said backing means; and handle means formed integrally as part of said label means to provide a user with a surface to grip said apparatus.

7. The apparatus for the containment and application of a product of claim 6 wherein said handle means comprises:

substantially rigid stiffener means for providing a surface that said user can grip said apparatus, said substantially rigid stiffener means being mounted to be substantially perpendicular to a major surface of said backing means, on a side opposite said means for controllable delivery.

8. The apparatus for the containment and application of a product of claim 6 wherein said packet means is, mounted in said handle means, stores a predetermined quantity of said product and wherein said packet means includes:

nozzle means for liquid communication through said aperture between said packet means and said means for controllable delivery for enabling passage of said product from said packet means to said means for controllable delivery in response to activation by said user.

9. The apparatus for the containment and application of a product of claim 1 wherein said means for controllable delivery comprises:

a deployable element which comprises an applicator for the application of said product to a desired surface, said deployable element being activatable by a user to switch from a first state where said applicator is protected from exposure to an ambient environment to a second state where said applicator is exposed to said ambient environment.

10. The apparatus for the containment and application of a product of claim 9 wherein said first state comprises said applicator folded against itself, clamshell style, and said second state comprises said applicator deployed substantially in a single planar surface, said backing means further comprises:

means for retaining said applicator in said first state.

11. The apparatus for the containment and application of a product of claim 10 wherein said backing means further comprises:

means, activatable by said user, for deactivating said means for retaining to enable deployment of said applicator.

12. The apparatus for the containment and application of a product of claim 1 wherein said means for controllable delivery comprises:

an applicator for the application of said product to a desired surface;

means for protecting said applicator from exposure to an ambient environment; and means, activatable by a user, for deactivating said means for protecting to enable exposure of said applicator to said ambient environment.

13. An apparatus for the containment and application of a product that has a one of liquid, semi-liquid, solid and semi-solid characteristics, comprising:

means, having a front surface and a back surface, for controllable delivery of said product via said front surface;

packet means for storing a predetermined quantity of said product, said packet means being rupturable to release said product upon application of a predetermined force thereon by a user;

means for covering said packet means and said means for controllable delivery to provide a barrier to release of said product; and an aperture formed in said means for covering for enabling placement of said packet means between said means for controllable delivery and said means for covering.

14. The apparatus for the containment and application of a product of claim 13 further comprising:

label means for substantially covering said aperture.

15. The apparatus for the containment and application of a product of claim 14 wherein said label means further comprises:

handle means formed integrally as part of said label means to provide a user with a surface to grip said apparatus.

16. The apparatus for the containment and application of a product of claim 15 wherein said handle means comprises:

substantially rigid stiffener means for providing a surface that said user can grip said apparatus, said substantially rigid stiffener means being mounted to be substantially perpendicular to a major surface of said label means, on a side opposite said means for controllable delivery.

17. The apparatus for the containment and application of a product of claim 13 wherein said means for controllable delivery comprises:

a deployable element which comprises an applicator for the application of said product to a desired surface, said deployable element being activatable by said user to switch from a first state where said applicator is protected from exposure to an ambient environment to a second state where said applicator is exposed to said ambient environment.

18. The apparatus for the containment and application of a product of claim 17 wherein said first state comprises said applicator folded against itself, clamshell style, and said second state comprises said applicator deployed substantially in a single planar surface, said means for covering further comprises:

means for retaining said applicator in said first state.

19. The apparatus for the containment and application of a product of claim 18 wherein said means for covering further comprises:

means, activatable by said user, for deactivating said means for retaining to enable deployment of said applicator.

20. The apparatus for the containment and application of a product of claim 13 wherein said means for controllable delivery comprises:

an applicator for the application of said product to a desired surface;

means for protecting said applicator from exposure to an ambient environment; and means, activatable by said user, for deactivating said means for protecting to enable exposure of said applicator to said ambient environment.

21. An apparatus for the containment and application of a product that has a one of liquid, semi-liquid, solid and semi-solid characteristics, comprising:

means, having a front surface and a back surface, for controllable delivery of said product via said front surface;

backing means, integrally attached to said back surface to form a product receiving site juxtaposed to said back surface, for providing a substantially impermeable barrier to said product;

an aperture opening into said product receiving site to enable placement of said product into said product receiving site through said aperture;

packet means for storing a predetermined quantity of said product, said packet means being at least partially insertable into said product receiving site through said aperture; and means for sealing said aperture after inserting said packet means.

22. The apparatus of claim 21 wherein said packet means is rupturable to release said product into said product receiving site upon application of a predetermined force thereon by a user.

23. The apparatus of claim 21 wherein said packet means stores a predetermined quantity of said product, and has a nozzle means in liquid communication through said aperture between an interior of said packet means and said means for controllable delivery, operable to enable passage of said product from said interior of said packet means to said means for controllable delivery in response to activation by said user.

24. The apparatus for the containment and application of a product of claim 21 wherein said means for sealing substantially covers said backing means and includes:

handle means formed integrally as part of said means for sealing to provide a user with a surface to grip said apparatus.

25. The apparatus for the containment and application of a product of claim 24 wherein said handle means comprises:

substantially rigid stiffener means for providing a surface that said user can grip said apparatus, said substantially rigid stiffener means being mounted to be substantially perpendicular to a major surface of said backing means, on a side opposite said means for controllable delivery.

26. The apparatus for the containment and application of a product of claim 24 wherein said packet means is mounted in said handle means, stores a predetermined quantity of said product and wherein said packet means includes:

nozzle means for liquid communication through said aperture between said packet means and said means for controllable delivery for enabling passage of said product from said packet means to said means for controllable delivery in response to activation by said user.

27. The apparatus for the containment and application of a product of claim 21 wherein said means for controllable delivery comprises:

a deployable element which comprises an applicator for the application of said product to said desired surface, said deployable element being activatable by a user to switch from a first state where said applicator is protected from exposure to an ambient environment to a second state where said applicator is exposed to said ambient environment.

28. The apparatus for the containment and application of a product of claim 27 wherein said first state comprises said applicator folded against itself, clamshell style, and said second state comprises said applicator deployed substantially in a single planar surface, said backing means further comprises:

means for retaining said applicator in said first state.

29. The apparatus for the containment and application of a product of claim 28 wherein said backing means further comprises:

means, activatable by said user, for deactivating said means for retaining to enable deployment of said applicator.

30. The apparatus for the containment and application of a product of claim 21 wherein said means for controllable delivery comprises:

an applicator for the application of said product to a desired surface;

means for protecting said applicator from exposure to an ambient environment; and means, activatable by a user, for deactivating said means for protecting to enable exposure of said applicator to said ambient environment.

* * * * *